(12) United States Patent
Scott et al.

(10) Patent No.: US 9,470,606 B2
(45) Date of Patent: Oct. 18, 2016

(54) SYSTEM FORCE-DEFORMATION MODELING APPARATUSES AND METHODS

(71) Applicant: Biodynamic Research Corporation, San Antonio, TX (US)

(72) Inventors: William R. Scott, San Antonio, TX (US); Enrique J. Bonugli, San Antonio, TX (US); Herbert M. Guzman, San Antonio, TX (US); Daniel J. Swartzendruber, San Antonio, TX (US)

(73) Assignee: BIODYNAMIC RESEARCH CORPORATION, San Antonio, TX (US)

( * ) Notice: Subject to any disclaimer, the term of this patent is extended or adjusted under 35 U.S.C. 154(b) by 0 days.

(21) Appl. No.: 14/805,576

(22) Filed: Jul. 22, 2015

(65) Prior Publication Data

US 2015/0330871 A1  Nov. 19, 2015

Related U.S. Application Data (63) Continuation of application No. 13/803,294, filed on Mar. 14, 2013.

(60) Provisional application No. 61/620,682, filed on Apr. 5, 2012.

(51) Int. Cl.
| | |
|---|---|
| *G01N 3/00* | (2006.01) |
| *G01M 17/007* | (2006.01) |
| *G01N 3/30* | (2006.01) |

(52) U.S. Cl.
CPC ............ *G01M 17/0078* (2013.01); *G01N 3/30* (2013.01)

(58) Field of Classification Search
CPC .............. G01M 17/0078; G01N 3/30; G01N 2203/0246
USPC ...................... 73/12.09, 12.04, 584, 862.381; 702/113; 324/691; 348/135
See application file for complete search history.

(56) References Cited

U.S. PATENT DOCUMENTS

| | | | | |
|---|---|---|---|---|
| 3,729,221 A | * | 4/1973 | Granig | B60R 21/34 293/117 |
| 5,485,758 A | * | 1/1996 | Brown | G01M 17/0078 73/12.04 |
| 6,658,336 B2 | * | 12/2003 | Browne | B60R 21/013 280/731 |
| 7,228,723 B2 | | 6/2007 | Evans et al. | 73/12.09 |
| 8,239,220 B2 | * | 8/2012 | Kidd | G01M 17/0078 705/305 |
| 2002/0013685 A1 | * | 1/2002 | Kidd | G06Q 99/00 703/8 |
| 2009/0171528 A1 | * | 7/2009 | Golde | G07C 5/0858 701/33.4 |
| 2013/0118226 A1 | * | 5/2013 | Young | G01N 3/30 73/12.01 |

OTHER PUBLICATIONS

Bailey, M.N., et al., Data and Methods for Estimating the Severity of Minor Impacts, SAE No. 950352, Warrendale, Pennsylvania 15096 (Apr. 2012).

(Continued)

*Primary Examiner* — Lisa Caputo
*Assistant Examiner* — Brandi Hopkins
(74) *Attorney, Agent, or Firm* — Norton Rose Fulbright US LLP (57) ABSTRACT

System force-deformation measuring apparatuses (e.g., an apparatus that applies a quasi-static force), such as those, for example, configured to generate data (e.g., non-generic or accident-specific data) that assists in the reconstruction of vehicle collisions.

21 Claims, 6 Drawing Sheets

(56) References Cited

OTHER PUBLICATIONS

Campbell, K., "Energy Basis for Collision Severity," SAE Technical Paper 740565, doi:10.4271/740565 (1974).

Cipriani, A.L., et al., Low Speed Collinear Impact Severity: A Comparison Between Full Scale Testing and Analytical Prediction Tools with Restitution Analysis, SAE No. 2002-01-0540, Warrendale, Pennsylvania 15096.

Happer, A.J., et al., Practical Analysis Methodology for Low Speed Vehicle Collisions Involving Vehicles with Modern Bumper Systems, SAE No. 2003-01-0492, Warrendale, Pennsylvania 15096.

W.R. Scott et al., Reconstruction of Low-Speed Crashes using the Quasi-Static Force vs. Deformation Characteristics of the Bumpers Involved in the Crashes, SAE No. 2012-01-0598.

W.R. Scott, et al., Simulation Model for Low-Speed Bumper-to-Bumper Crashes, SAE No. 2010-01-0051 (Apr. 2010).

* cited by examiner

SYSTEM FORCE-DEFORMATION MODELING APPARATUSES AND METHODS

CROSS-REFERENCE TO RELATED APPLICATIONS

This application is a continuation of U.S. patent application Ser. No. 13/803,294 filed Mar. 14, 2013, and U.S. Provisional Patent Application No. 61/620,682, filed Apr. 5, 2012, both of which are incorporated herein by reference in their entireties.

BACKGROUND

1. Field of the Invention

The present invention relates generally to impact or collision modeling and, more particularly, but not by way of limitation, to generating data (e.g., non-generic or accident-specific data) that can be used in accident-reconstruction techniques that can be used to model low-speed vehicle (e.g., automobile) collisions.

2. Description of Related Art

An example of an impact-modeling apparatus and method is disclosed in W. R. Scott, et al., *Simulation Model for Low-Speed Bumper-to-Bumper Crashes*, SAE International, 2010 World Congress & Exhibition, SAE No. 2010-01-0051 (April 2010) and W. R. Scott, et al., *Reconstruction of Low-Speed Crashes using the Force vs. Deformation Characteristics of the Bumpers Involved in the Crashes*, SAE International, 2012 World Congress & Exhibition, SAE. No. 2012-01-0598.

SUMMARY

This disclosure includes embodiments of impact-modeling apparatuses (e.g., an apparatus that measures the quasi-static force-deformation characteristics of the structures on each vehicle that contacts and sustains damage in a vehicle collision). In some embodiments, contacting structures in a low-speed collision are treated as a system. For example, if modeling a two-car low-speed collision, the system will generally comprise two bumpers; but the system can also comprise other components, such as a bumper and a fender. One unique advantage of the present apparatuses and methods (e.g., for accident reconstruction) is that the data obtained are not generic, that is, the data are particularly applicable and representative of a single crash event being investigated, which can result in a much higher level of precision in determining vehicle crash accelerations than prior reconstruction techniques that use generic data.

Some embodiments of the present apparatuses comprise: a frame; a mount movably coupled to the frame, the mount configured to be coupled to a vehicle bumper; and an actuator configured to move the mount relative to the frame; where the apparatus is configured to be actuated to compress a vehicle bumper between the mount and the frame. Some embodiments further comprise: a vehicle bumper coupled to the mount. In some embodiments, the actuator comprises at least one hydraulic cylinder. In some embodiments, the at least one hydraulic cylinder has a first end configured to be coupled to the mount, and a second end configured to be coupled to the frame. Some embodiments further comprise: at least one sensor configured to detect a force applied to the mount by the actuator. In some embodiments, the sensor is configured to be coupled to at least one of the mount and the actuator. Some embodiments further comprising a plurality of sensors configured to measure a force applied to the mount by the actuator. In some embodiments, at least one sensor is disposed between the mount and the actuator such that the sensor can detect a force applied to the mount by the actuator.

In some embodiments of the present apparatuses, the mount comprises at least one reinforcement bar configured to be coupled to a vehicle bumper. In some embodiments, the at least one reinforcement bar is substantially rigid. In some embodiments, the at least one reinforcement bar is removably coupled to the mount. In some embodiments, the at least one reinforcement bar is unitary with the mount. Some embodiments further comprising at least one sensor coupled to the at least one reinforcement bar such that the at least one sensor can measure a force applied to the reinforcement bar. In some embodiments, the mount comprises load-bearing rollers configured to roll in contact with the frame when the mount moves relative to the frame. In some embodiments, the mount has at least an outer dimension of at least 3 feet. In some embodiments, the frame has at least an outer dimension greater than 5 feet. In some embodiments, the frame will not fit within a rectangular volume of 45 ft$^3$. In some embodiments, the frame will fit within a rectangular volume of 250 ft$^3$. In some embodiments, the actuator comprises one or more items selected from the group consisting of: a motor, a screw jack, a ball screw, roller screw, a hoist, a winch, a rack and pinion, a chain drive, a belt drive, a rigid chain, and a rigid belt. In some embodiments, the actuator is configured to apply a force of at least 5,000 pounds. In some embodiments, the actuator is configured to move the mount at a rate of less than 3 feet per second. In some embodiments, the actuator is configured to move the mount at a rate of less than 0.1 feet per second.

Some embodiments of the present apparatuses further comprises: at least one displacement sensor configured to measure displacement of the mount relative to the frame. In some embodiments, the at least one displacement sensor is coupled to the mount. In some embodiments, the at least one displacement sensor is coupled to the frame. In some embodiments, at least one image sensor is configured to record images of the apparatus. In some embodiments, at least one audio sensor is configured to detect sounds during use of the apparatus. In some embodiments, the mount is configured to be coupled to a vehicle bumper with the vehicle bumper in any of various positions relative to the frame. Some embodiments further comprise: a second mount coupled in fixed relation to the frame, the second mount configured to be coupled to a vehicle bumper, where the apparatus is configured to be actuated to compress two vehicle bumpers between the first and second mounts. Some embodiments further comprise: a first vehicle bumper coupled to the first mount, and a second vehicle bumper coupled to the second mount. Some embodiments further comprise: a controller configured to actuate the actuators to move the mount at a rate of less than 1 foot per minute with a force of greater than 5,000 pounds.

Some embodiments of the present apparatuses comprise: a frame; a first mount coupled in fixed relation to the frame, the first mount configured to be coupled to a vehicle bumper; a second mount movably coupled to the frame, the second mount configured to be coupled to a vehicle bumper; and an actuator configured to move the second mount relative to the frame; where the apparatus is configured to be actuated to compress at least one vehicle bumper between the first and second mounts. Some embodiments further comprise: a vehicle bumper coupled to the first and second mounts. In some embodiments, the actuator comprises at least one hydraulic cylinder. In some embodiments, the at least one hydraulic cylinder has a first end configured to be coupled to the second mount, and a second end configured to be coupled to the frame. Some embodiments further comprise: at least one sensor configured to detect a force applied by the actuator to at least one of the first and second mounts. In some embodiments, the sensor is configured to be coupled to at least one of the first mount, the second mount, and the actuator. Some embodiments further comprising a plurality of sensors configured to measure a force applied by the actuator to at least one of the first and second mounts. In some embodiments, at least one sensor is disposed between the second mount and the actuator such that the sensor can detect a force applied to the second mount by the actuator. In some embodiments, the first and second mounts comprise at least one reinforcement bar configured to be coupled to a vehicle bumper. In some embodiments, the at least one reinforcement bar is substantially rigid. In some embodiments, the at least one reinforcement bar is removably coupled to at least one of the first and second mounts. In some embodiments, the at least one reinforcement bar is unitary with at least one of the first and second mounts. Some embodiments further comprise: at least one sensor coupled to the at least one reinforcement bar such that the at least one sensor can measure a force applied to the at least one reinforcement bar. In some embodiments, the second mount comprises load-bearing rollers configured to roll in contact with the frame when the second mount moves relative to the frame.

In some embodiments of the present apparatuses, the first and second mounts have an outer dimension of at least 3 feet. In some embodiments, the frame has at least an outer dimension greater than 5 feet. In some embodiments, the frame will not fit within a rectangular volume of 45 ft$^3$. In some embodiments, the frame will fit within a rectangular volume of 250 ft$^3$. In some embodiments, the actuator comprises one or more items selected from the group consisting of a motor, a screw jack, a ball screw, roller screw, a hoist, a winch, a rack and pinion, a chain drive, a belt drive, a rigid chain, and a rigid belt. In some embodiments, the actuator is configured to apply a force of at least 5,000 pounds. In some embodiments, the actuator is configured to move the second mount at a rate of less than 3 feet per second. In some embodiments, the actuator is configured to move the second mount at a rate of less than 0.1 feet per second. Some embodiment further comprise: at least one displacement sensor configured to measure displacement of the second mount relative to the frame. In some embodiments, the at least one displacement sensor is coupled to the second mount. In some embodiments, the at least one displacement sensor is coupled to the frame. In some embodiments, at least one image sensor is configured to record images of the apparatus. In some embodiments, at least one audio sensor is configured to detect sounds during use of the apparatus. In some embodiments, the first and second mounts are configured to be coupled to a vehicle bumper with the vehicle bumper in any of various positions relative to the frame. Some embodiments further comprise: a controller configured to actuate the actuators to move the mount at a rate of less than 0.1 foot per minute with a force of up to 50,000 pounds.

Some embodiments of the present methods (e.g., for modeling damage to a vehicle bumper) comprise: (i) applying and releasing a first quasi-static force to a system; (ii) determining whether the quasi-static force caused a permanent deformation of a component of the system; (iii) if the quasi-static force caused a permanent deformation, comparing the permanent deformation to a reference deformation; (iv) if the first quasi-static force did not cause a permanent deformation or caused a permanent deformation that is less than the reference deformation, applying and releasing a subsequent quasi-static force to the system; and (v) repeating steps (i)-(iii) until a permanent deformation of the component equals or exceeds the reference deformation. Some embodiments further comprise: collecting at least one of displacement and force data during the application and release of the quasi-static force to the system. Some embodiments further comprise: collecting displacement and force data corresponding to the quasi-static force that results in a permanent deformation of the component that equals or exceeds the reference deformation. Some embodiments further comprise: generating a compression and rebound curve from the displacement and force data. Some embodiments further comprise: using the compression and rebound curve to determine an impact velocity. Some embodiments further comprise: using the compression and rebound curve to determine a coefficient of restitution.

Some embodiments of the present methods comprise applying a quasi-static force to a system using any embodiment of the present apparatuses. Some embodiments further comprise modeling a dynamic force-deformation function with a quasi-static force-deformation function. Some embodiments further comprise reconstructing a low-speed crash using quasi-static force-deformation characteristics. Some embodiments further comprise determining an impact force in a low-speed crash by comparing damage in a reference object (e.g., a bumper) to damage in an object to which the quasi-static force was applied (e.g., a bumper).

Any embodiment of any of the present apparatuses can consist of or consist essentially of—rather than comprise/include/contain/have—any of the described elements and/or features. The same is true of the present methods. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present impact modeling apparatuses and their components shown in the figures are drawn to scale for at least the depicted embodiment.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a bumper system force-deformation measuring apparatus, or a component of such an apparatus, that is configured in a certain way is configured in at least that way, but it can also be configured in other ways than those specifically described.

1. Theoretical Overview

Many crash reconstruction techniques have been developed over the last forty years that use the crush damage to reconstruct the crash. These damage-based reconstruction techniques are based on the principle that the impact forces that act on a vehicle in a collision are proportional to the crush of the vehicle. The initial damage based accident reconstruction techniques were developed by the National Highway Transportation Safety Administration (NHTSA). The NHTSA needed methods to estimate the severity of crashes so that field data could be used to evaluate the new Federal Motor Vehicle Safety Standards (FMVSS). The variable that was selected to represent crash severity in frontal and rear crashes was the change in velocity ($\Delta V$) experienced by the vehicles in the crash. These reconstruction methods generally use generic information to represent stiffness characteristics of a vehicle in a crash and may work well for high speed crashes, where there are many inches of uniform crush on the collision vehicles. However, traditional reconstruction methods do not work well for low-speed crashes. Low-speed crashes are generally defined as collisions where the $\Delta V$ each vehicle experiences is approximately 10 mph or less. In a low-speed crash, there may be no measurable crush or limited areas of focal damage that are difficult to quantify. In many cases, the only information about damage to each vehicle is photographs of the vehicles and repair estimates, with no physical measurements.

Two methods have been used to reconstruct low-speed crashes but both methods are limited because at present there is no technique to accurately quantify the damage created in the crash that is being investigated. The first method, the spring/dashpot method, treats the vehicles as rigid structures and the bumpers are modeled as spring/dashpots. The spring/dashpot model requires the stiffness and damping coefficients for these theoretical bumpers interacting in the crash. These coefficients are generally not known. The governing differential equations with the appropriate initial conditions may then be solved. The calculated solution provides the accelerations experienced by the vehicles in the crash and the calculated crush (or damage), which is uniform across the contact area for each vehicle. In most low-speed crashes the crush is not uniform, so this calculated crush does not reflect the non-uniform damage patterns that vehicles experience in real crashes. With this reconstruction process there is no metric to compare the calculated or simulated crash with the real world crash and determine the accuracy of the reconstruction.

The second method for reconstructing low-speed crashes is the Momentum-Energy-Restitution (MER) method. The MER method uses impulse, conservation of momentum, conservation of energy, and restitution to determine the change in velocity ($\Delta V$) of each of the vehicles involved in the crash. In order to estimate the $\Delta V$ for a vehicle, the MER method requires a value for the coefficient of restitution (C) of the crash (a measure of the elasticity of the crash) and an estimate of the energy absorbed by both vehicles in the crash. While there are methods to estimate C, it is difficult, if not impossible, to determine the amount of energy absorbed by both vehicles during a crash by looking at photographs. Furthermore, the calculation in the MER method provides no damage estimate so there is no metric within the calculation to estimate how well the analysis represents the real world crash.

The quasi-static force-deformation data produced by the force-deformation measuring apparatus allows a third method to be used is reconstructing low-speed impacts as it has been shown that the quasi-static force-deformation characteristics measured with the system force-deformation measuring apparatus may be used to represent the dynamic force-deformation characteristics of structures that contact and deform in a low-speed impact [2]. Therefore, Newton's Three Laws of Physics can be solved at discrete time steps in a numerical simulation of the crash and the accelerations of each vehicle during the crash can be calculated. A simulation model, called the Low-Speed Simulation, was developed previously with the idea of using data from a device, such as the system force-deformation measuring apparatus [1]. The $\Delta V$ for each vehicle in this simulation is determined by integrating the accelerations of each vehicle over the period of the crash. The system force-deformation measurement also creates a damage pattern on the system components similar to the reference damage (e.g., the damage pattern on components in the crash being investigated). A visual or photographic comparison of the damage pattern for the system components with the reference damage provides a method to determine the accuracy of the simulation of the crash.

Figure 1:
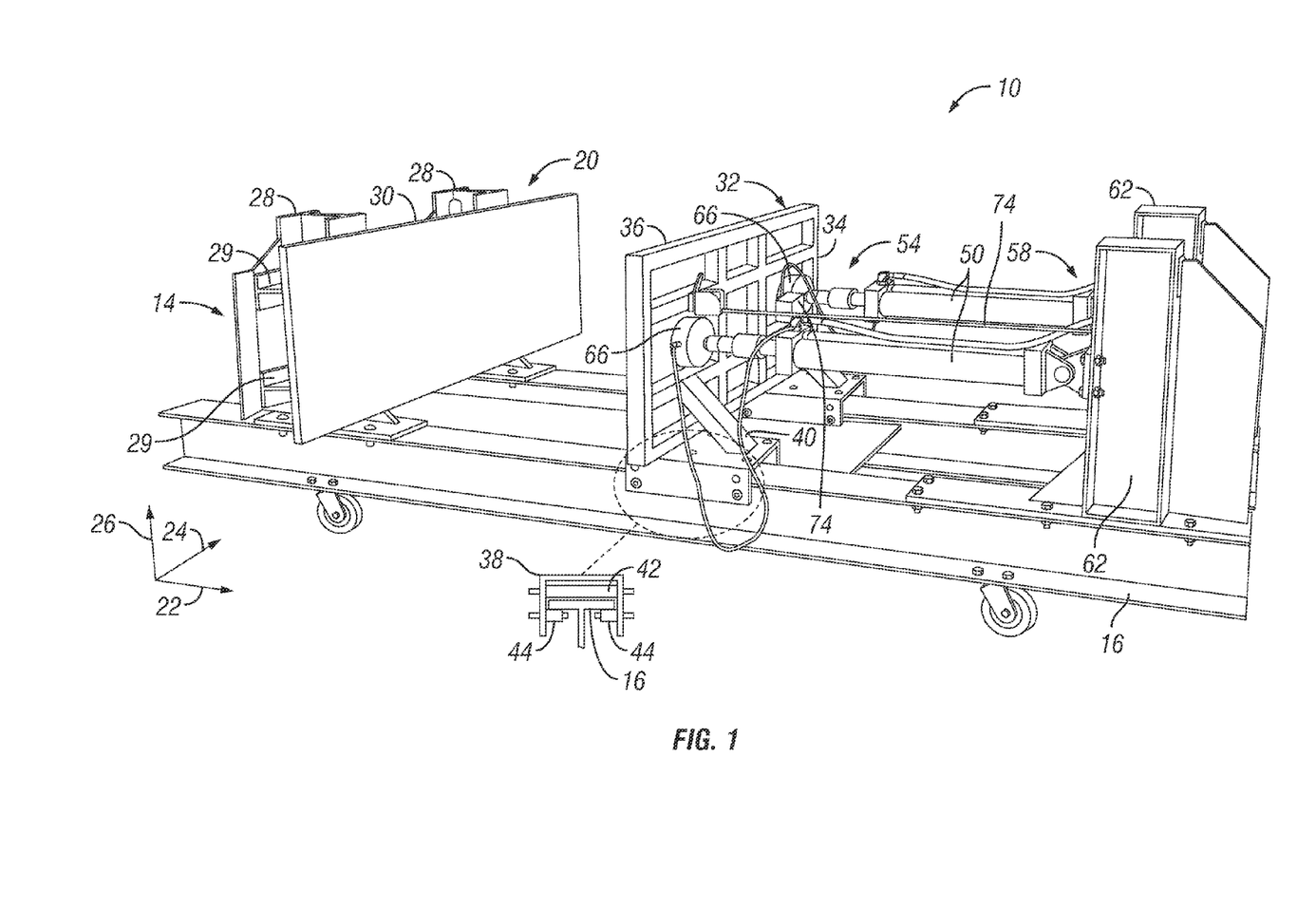
FIG. 1 depicts a perspective view of an embodiment of the present system force-deformation measuring apparatuses having a first mount and a second mount, shown without a vehicle component coupled to the mounts.
Figure 2:
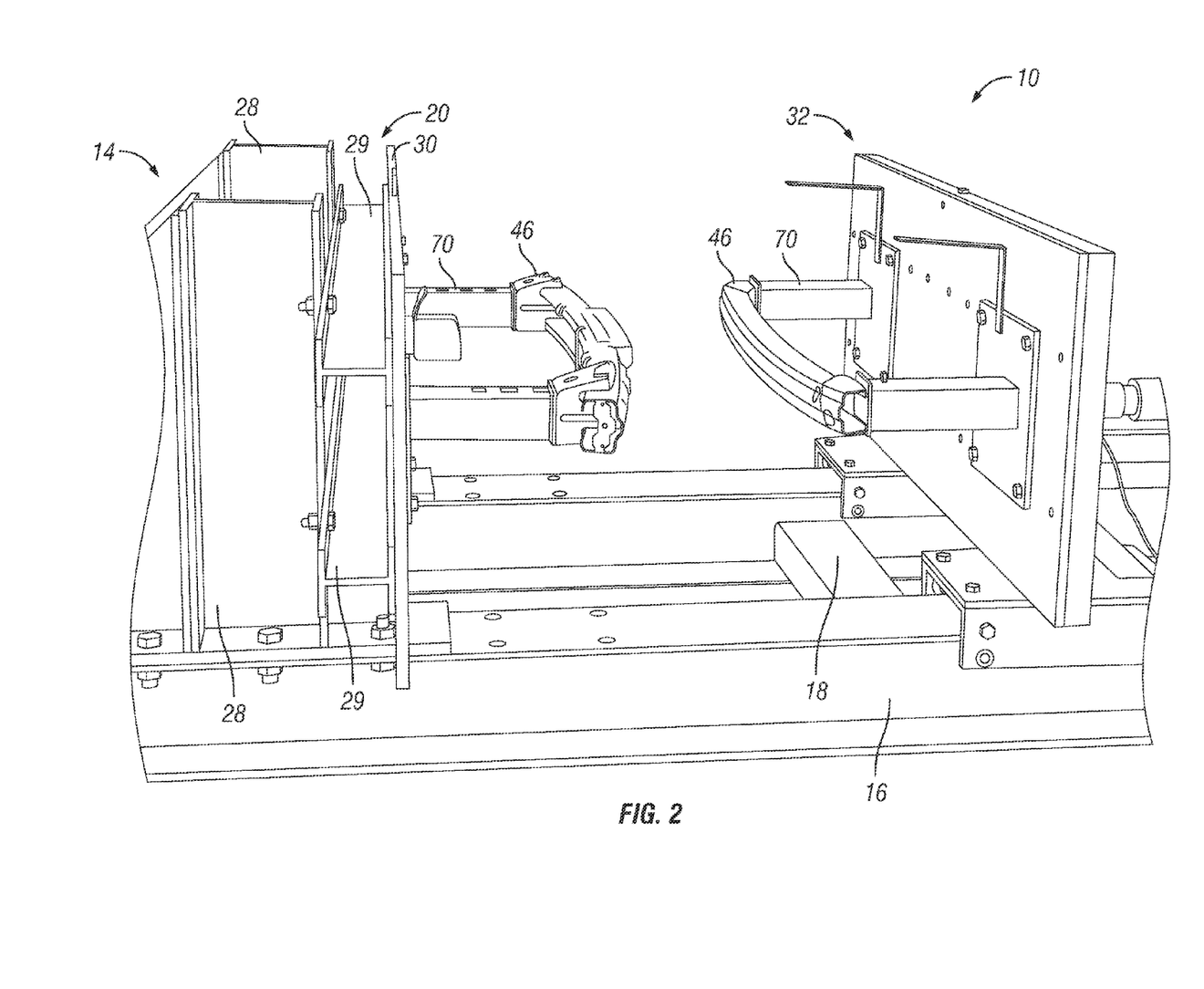
FIG. 2 depicts a side elevation view of the apparatus of FIG. 1 with a reinforcement bar from a bumper coupled to each of the first mount and the second mount.
Figure 3:
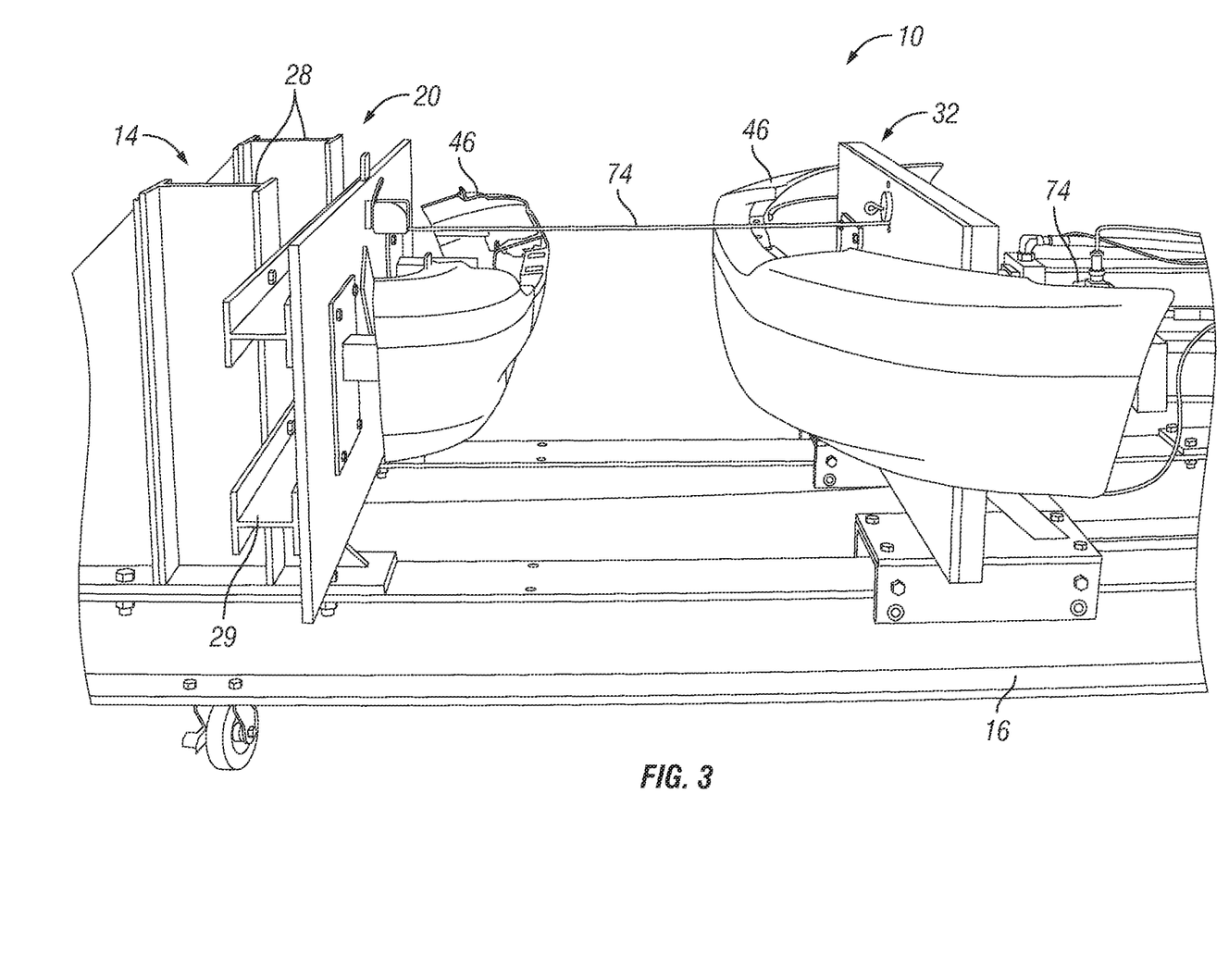
FIG. 3 depicts a close-up side elevation view of the apparatus of FIG. 1 with a complete bumper coupled to each of the first mount and the second mount.
Figure 4:
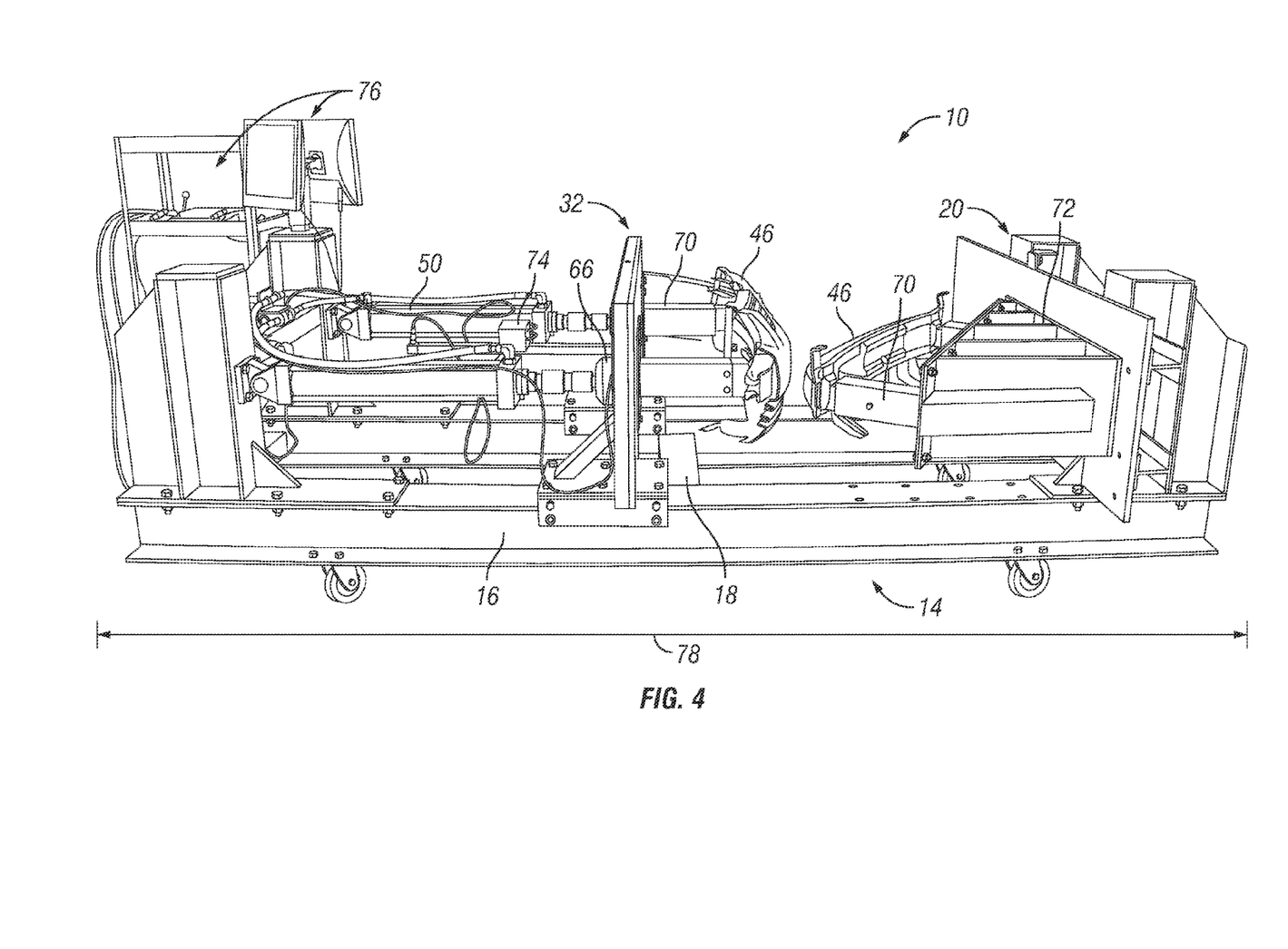
FIG. 4 depicts a side elevation view of the apparatus of FIG. 1 with reinforcement bars disposed at an angle on the mount allowing for a vehicle bumper to be disposed in any of various positions relative to the frame of the apparatus.
Figure 5:
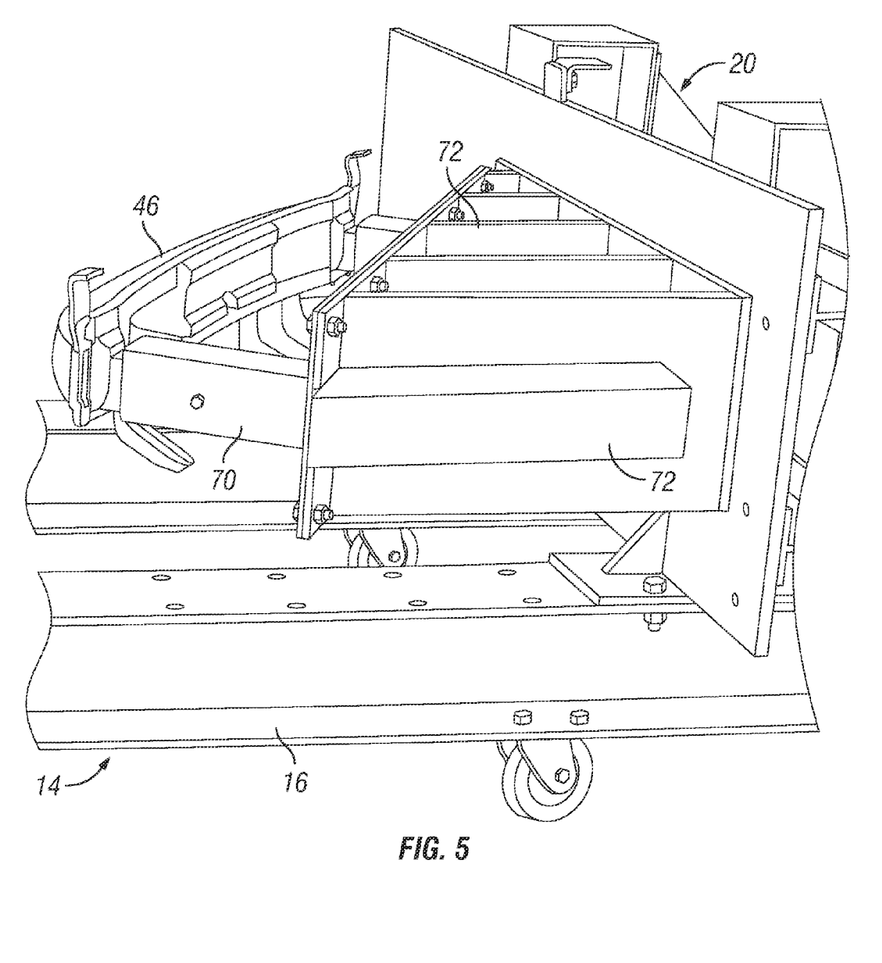
FIG. 5-7 depict detailed views of various components of FIG. 4.
Figure 6:
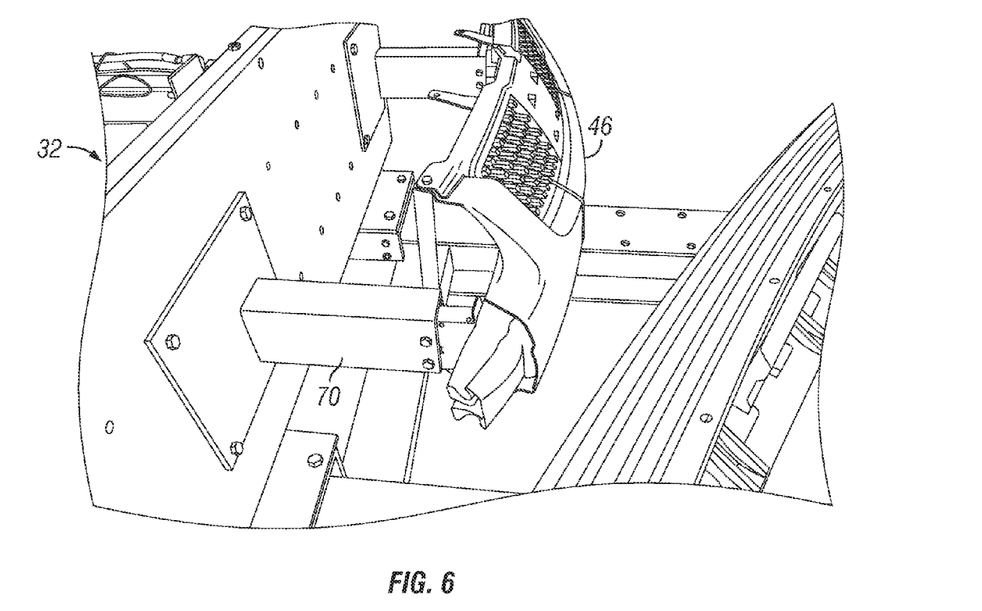
Figure 7:
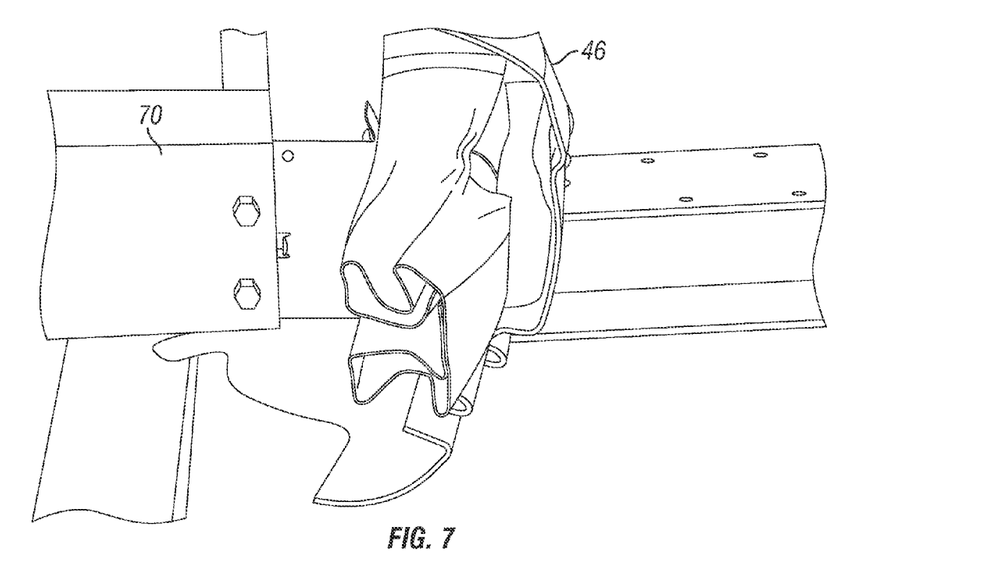

The force-deformation characteristics of the system are measured in the device shown in FIG. 1, the system force-deformation measuring apparatus. The measurement device has two steel plates, one is movable and the other is rigidly attached to the frame. Hardware that represents the frame or unibody attachment point of the bumper or other component that makes up the system is bolted to each plate. The components of the system are mounted to this hardware with the OEM (original equipment manufacturer) brackets. The alignment of the components, both vertical and horizontal, is determined from the damage pattern to the components in the subject crash and/or from an exemplar vehicle matchup. Once mounted, the components are slowly pushed into each other at a speed of approximately 0.5 inches per second. Because of the slow rate of compression the data are considered to be quasi-static. Quasi-static is defined as much slower than the closing velocity of vehicles in a low-speed crash, which is approximately 15 mph or less. The closing speed is defined as the speed difference between two vehicles at the time of initial contact. As components of the system are being pushed together the compression force and the deformation of the system are measured. The system deformation is the sum of the deformation of the two components that make up the system. If the components are aligned as they were in the subject crash, damage to components in the system that were subject to the force-deformation measuring apparatus should be similar to damage to components in the actual crash. During the measurement, an operator of the apparatus can decide when damage is similar by, for example, a visual comparison with photographs or photogrammetry. Once the measurement is complete, permanent deformation of the system components is preserved in the test components.

2. Structural Overview

Embodiments of the present apparatuses can be configured to quasi-statically apply force and/or crush at least one test component (e.g., bumper) in a desired orientation. A variety of data can be measured to determine characteristics of the component under the applied force, such as, for example, to determine a force and/or range of possible forces applied to a similar component during a low-speed collision. The apparatuses and methods may also be applied to any relevant part of a vehicle (e.g., a bumper, a fender, a grill, etc.).

FIGS. 1-5 depict an embodiment 10 of the present apparatuses. In the embodiment shown, apparatus 10 comprises a frame 14 (e.g., steel bars, iron bars, etc.). In the embodiment shown, frame 14 includes two longitudinal members 16 that each comprises a steel I-beam, and transverse members 18 are substantially perpendicular to longitudinal members 16. In other embodiments, frame 14 can include any suitable number and orientation of transverse members (e.g., two, three, or more at any suitable angle relative to longitudinal members 16).

In the embodiment shown, apparatus 10 comprises a first mount 20 (e.g., a steel plate, an iron plate, etc.) coupled in fixed relation (e.g., not movable) to frame 14. In other embodiments, first mount 20 may be movable relative to frame 14. For example, the first mount can be configured to move longitudinally in an X direction 22 (shown parallel to longitudinal members 16), laterally in a Y direction 24 (shown parallel to transverse member 18), and/or vertically in a Z direction 26 (shown perpendicular to longitudinal members 16 and transverse member 18). In the embodiment shown, first mount 20 comprises two vertical members 28 each coupled (e.g., via bolts, welds, and/or the like) in fixed relation to two transverse members 29. Each of vertical members 28 is also coupled in fixed relation to one of longitudinal members 16. In the embodiment shown, first mount 20 also comprises plate 30 extending across and coupled in fixed relation to transverse members 29. In the embodiment shown, vertical members 28 and transverse members 29 are oriented such that plate 30 is substantially vertical (parallel to direction 26). In the embodiment shown, each of vertical members 28 and transverse members 29 comprises a steel I-beam.

In the embodiment shown, apparatus 10 further comprises a second mount 32 movably coupled (e.g., slidably, rollably, etc.) to frame 14 in a X direction 22. In other embodiments, second mount 32 may be movable relative to frame 14 in other directions (e.g., second mount 32 may, additionally or alternatively, be movable in Y direction 24 and/or Z direction 26 relative to frame 14). In the embodiment shown, second mount 32 comprises a cross-braced frame 34, a plate 36 coupled in fixed relation to frame 34, two inverted channel-iron members 38 each movably coupled to one of longitudinal members 16, and two braces 40 each extending between frame 34 and one of members 38. In the embodiment shown, second mount 32 also comprises load-bearing rollers 42 configured to roll in contact with frame 14 (e.g., in contact with upper flanges of longitudinal members 16) when second mount 32 moves relative to frame 14. In the embodiment shown, second mount 32 also includes retainer rollers 44 configured to prevent second mount 32 from moving vertically (in direction 26) away from the frame. For example, in the embodiment shown, retainer rollers 44 extend inward from member 38 and below the upper flanges of longitudinal members 16 of the frame. In some embodiments, such as those in which first mount 20 is movably coupled to the frame, first mount 20 also comprises load-bearing rollers 42 and/or retainer rollers 44.

In the embodiment shown, first and second mounts 20 and 32 are each configured to be coupled (e.g., removably) to at least one of a vehicle bumper 46 or another object (e.g., representative of an object involved (e.g., directly contacted) in a crash or collision, such as, for example, a section of a telephone or light pole, a bollard, a wall, a vehicle component other than a bumper, or the like). In the embodiment shown, each of first and second mounts 20 and 32 are coupled to a different vehicle bumper 46. In the embodiments shown, first and mounts 20 and 32 have at least one outer dimension of at least 3 feet (e.g., 3 feet, 4 feet, or more). For example, in the embodiment shown, each of the first and second mounts 20 and 32 has a maximum width (in direction 24) equal to or greater than 5 feet.

In the embodiment shown, apparatus 10 comprises at least one (e.g., two, as shown) actuator 50 (e.g., a hydraulic cylinder, motor, screw jack, etc.) configured to move second mount 32 relative to frame 14 (e.g., in direction 22 along longitudinal member 16). In some embodiments, actuators 50 may be configured to move first mount 20 and/or second mount 32 relative to frame 14. For example, in the embodiment shown, actuators 50 are configured to be activated together to move second mount 32 relative to frame 14 and relative to first mount 20, such that apparatus 10 can be actuated to compress components of the system (e.g., bumpers 46) between first mount 20 and second mount 32. In some embodiments, apparatus 10 may be configured to be actuated to compress at least one vehicle bumper 46 between one of first mount 20 and second mount 32 and frame 14 (e.g., in some embodiments, apparatus 10 may comprise only one of first mount 20 and second mount 32). For example, in the embodiment shown, bumpers 46 are coupled to first mount 20 and second mount 32 such that both bumpers can be compressed (e.g., collided) between the first and second mounts.

In the embodiment shown, each actuator 50 comprises a hydraulic cylinder. In the embodiment shown, at least one hydraulic cylinder has a first end 54 configured to be coupled to second mount 32 and a second end 58 configured to be coupled to frame 14. More particularly, in the embodiment shown, frame 14 includes members 62, each coupled to one of longitudinal members 16 and to which second end 58 of one of the actuators is configured to be coupled (and are shown coupled). In this embodiment, each of members 62 comprises a steel I-beam that is coupled in fixed relation to, and substantially perpendicular to, one of longitudinal members 16. In this embodiment, members 62 have a height in direction 26 that is sufficient to permit actuators 50 to be substantially parallel to longitudinal members 16. In some embodiments, one or more of actuators 50 can comprise one or more items selected from the group consisting of a motor, a screw jack, a ball screw, roller screw, a hoist, a winch, a rack and pinion, a chain drive, a belt drive, a rigid chain, and a rigid belt.

In the embodiment shown, actuator 50 is configured to apply a force of at least 5,000 pounds. In some embodiments, actuator 50 may be configured to apply a force of greater than 5,000 pounds (e.g., 10,000 pounds, 20,000 pounds, or more). In other embodiments, actuator 50 may be configured to apply a force of less than 5,000 pounds (e.g., 4,000 pounds, 3,000 pounds, or less). In the embodiment shown, actuator 50 may be configured to move second mount 32 at a rate of less than 3 feet per second (e.g., 2 ft/s, 1 ft/s, 0.5 ft/s, 0.05 ft/s, or less). In some embodiments, actuator 50 may be configured to move first mount 20 and/or second mount 32 at a rate of less than 3 feet per second (e.g., 2 ft/s, 1 ft/s, 0.5 ft/s, 0.05 ft/s, or less).

In the embodiment shown, apparatus 10 further comprises at least one sensor 66 coupled to first end 54 of the at least one hydraulic cylinder and configured to detect a force applied to first mount 20 and/or second mount 32 by actuator 50. For example, in the embodiment shown, the apparatus comprises two sensors 66, each comprising a load cell disposed between second mount 32 and first end 54 of one of the actuators. In some embodiments, at least one sensor 66 is configured to detect a force applied to and components of the system, such as at least one vehicle bumper 46. In some embodiments, sensor 66 is configured to be coupled to at least one of mounts 20 and 32 and actuator 50. In some embodiments, apparatus 10 may comprise a plurality of sensors 66 configured to measure a force applied to at least one of mounts 20 and 32 by actuator 50. In the embodiment shown, at least one sensor 66 is disposed between second mount 32 and actuator 50 such that at least one sensor 66 can detect a force applied to second mount 32 by the at least one actuator 50. In some embodiments, at least one sensor 66 is disposed between at least one of mounts 20 and 32 such that at least one sensor 66 can detect a force applied to at least one of mounts 20 and 32 by actuator 50. In the embodiment shown, sensor 66 can directly measure or detect the force applied by actuator 50 to mount 32, and can indirectly measure or detect the force between a test object (e.g., a first bumper) coupled to mount 20 and another object (e.g., a second bumper) with which the test object interacts (e.g., by directly contacting).

In the embodiment shown, at least one of mounts 20 and 32 comprise at least one bar 70 configured to be coupled (e.g., removably) to vehicle bumper 46. In the embodiment shown, each bar 70 is substantially rigid (e.g., bar 70 will substantially not deform under at least some forces that will cause vehicle bumper 46 to deform). In the embodiment shown, each bar 70 is removably coupled (e.g., with bolts, latches, etc.) to one of mounts 20 and 32 and to a bumper 46 or other test object. In some embodiments, each bar 70 is unitary with the mounts to which it is coupled. In some embodiments, a length of bar 70 can be selected to dispose the respective vehicle bumper 46 at any of various positions (e.g., horizontally, etc.) relative to frame 14 (e.g., mount 32). For example, in the embodiment shown in FIGS. 4 and 5, a bumper 46 can be coupled to mount 32 with two bars 70 and a brace 72 to simulate an angular relationship between two cars when simulating a low-speed collision. As in the embodiment shown and displayed in FIGS. 4 and 5, bars 70 can be coupled to a mount or a brace at any of a variety of positions to dispose a first test bumper coupled to mount 20 at any of a variety of orientations (e.g., center to center, left side to center, left side to right side, etc.) relative to a second test bumper coupled to mount 32. For example, the test bumpers can be coupled to the mounts to simulate cars of different heights colliding at any of a variety of angular orientations therebetween to obtain a point of contact between the two bumpers that is representative of the point of contact between the two types of bumpers when collided between the types of cars to which the test bumpers would otherwise be coupled. In some embodiments, at least one sensor 66 is coupled to at least one bar 70 such that at least one sensor 66 can measure a force applied to bar 70.

In the embodiment shown, apparatus 10 comprises at least one displacement sensor 74 (e.g., transducer, string pot (string potentiometer), LVDT, etc.) configured to measure displacement of at least one of mounts 20 and 32 relative to frame 14. In the embodiment shown, displacement sensor 74 includes a string pot that is coupled between mounts 20 and 32. Displacement sensor 74 can also be coupled between mount 32 and vertical member 62 of frame 14 (e.g., as depicted in FIG. 1). In the embodiment shown, displacement sensor 74 further comprises an LVDT. In other embodiments, the displacement sensor can be coupled in any suitable position and/or configuration to enable the displacement sensor to measure the movement of mount 20, a distance between mounts 20 and 32, and/or the objects that are coupled to the mounts. For example, in some embodiments, at least one displacement sensor 74 is coupled to frame 14, and/or to at least one vehicle bumper 46 configured to measure displacement of vehicle bumper 46 relative to frame 14 and/or mounts 20 and 32.

In some embodiments, apparatus 10 can comprise and/or be used with various additional sensors. In some embodiments, at least one image sensor (e.g., a video camera) can be configured to record images of apparatus 10 (e.g., of at least one test bumper moving in the apparatus). In some embodiments, at least one audio sensor (e.g., a sound recorder) can be configured to detect sounds during use of apparatus 10. In other embodiments, apparatus 10 may comprise a controller 76 (e.g., a computer in FIG. 4). In the embodiment shown, controller 76 is configured to actuate the at least one actuator. In some embodiments, controller 76 is configured to actuate at least one actuator 50 to move at least one of mounts 20 and 32 at a rate of less than 2 inches per second (e.g., 2 in/s, 1 in/s, 0.5 in/sec, or less) with a force of up to 50,000 pounds (e.g., 10,000 pounds, 20,000 pounds, 30,000 pounds, 40,000 pounds, or more). In some embodiments, controller 76 may comprise a variety of software and/or programs (e.g., MATLAB, S-PLUS, LabVIEW, IDL, etc.) configured to collect data obtained from use of apparatus 10 and further configured to compute and/or calculate results consistent with the methods of using apparatus 10.

In the embodiment shown, frame 14 has at least an outer dimension (e.g., length 78 greater than 5 feet). In the embodiment shown, frame 14 will not fit within (e.g., is larger than) a rectangular cylinder volume of 45 ft$^3$. In the embodiment shown, frame 14 will fit within a rectangular volume of 250 ft$^3$.

Some embodiments of the present methods include using embodiments of the present apparatuses (e.g., 10). One of the present methods includes using the present apparatuses for modeling damage to a system that includes, for example, vehicles and components of vehicles, such as vehicle bumper 46, and comprises: (i) defining the system (e.g., objects in a crash (e.g., vehicles, bumpers, and the like), the objects orientations relative to one another in the crash, etc.), (ii) applying and releasing a first quasi-static force to the system; (iii) determining whether the quasi-static force caused a permanent deformation of the system (e.g., in one or more components of the system); (iv) if the quasi-static force caused a permanent deformation, comparing the permanent deformation to a reference deformation; (v) if the first quasi-static force did not cause a permanent deformation or caused a permanent deformation that is less than the reference deformation, applying and releasing a subsequent quasi-static force to the system; (vi) repeating steps (ii) and (iii) until a permanent deformation of the system equals or exceeds the reference deformation. In some embodiments, the method may comprise collecting at least one of displacement and force data (e.g., via sensor 66 and/or sensor 74) during the application and/or release of the quasi-static force to the bumper 46. In some embodiments, the method may comprise collecting displacement and force data corresponding to the quasi-static force that results in a permanent deformation of the system that equals or exceeds the reference deformation. In some embodiments, the method may comprise generating a compression and rebound curve from the displacement and force data; and, optionally, determining an impact velocity and/or a coefficient of restitution from the compression and rebound curve. In some embodiments, the method may comprise modeling a dynamic force-deformation function with a quasi-static force-deformation function. In some embodiments, the method may comprise reconstructing a low-speed crash using quasi-static force-deformation characteristics. In some embodiments, the method may comprise determining a peak impact force in a low-speed crash by comparing damage in a reference bumper (a bumper involved in the low-speed crash) to the damage to a vehicle bumper 46 (test bumper).

3. Examples

The following includes examples of how the present embodiment of the force-deformation measuring apparatus can be used to reconstruct low-speed collisions. One method is to use the quasi-static force-deformation data in a low-speed simulation model that calculates the vehicle accelerations and velocities during a collision and provides the $\Delta V$ for each vehicle during the collision. A detailed description of the methods and techniques used in this method is provided in references 1 and 2. A second method that can use the quasi-static force-deformation data is the MER method for reconstructing low-speed collisions. In the MER method the quasi-static force-deformation data is used to calculate the crush energy of the collision and to assist in the calculation of the $\Delta V$ of each vehicle involved in the collision.

In the "Reconstruction of Low-Speed Crashes Using the Quasi-Static Force vs. Deformation Characteristics of the Bumpers Involved in the Crashes" three component systems were evaluated to confirm that quasi-static force-deformation data could be used to model a real world crash [2]. Each component system was made up of two bumpers, and was called a bumper system in this validation study. In this validation study, a series of quasi-static force-deformation measurements were made on the three bumper systems using the force-deformation measuring apparatus. In this validation study, the quasi-static force-deformation data for each bumper system was obtained by pushing two bumpers of the bumper system into each other using the force-deformation measuring apparatus. The bumper system included the rear original equipment manufacturer (OEM) bumper from a rear-ended vehicle and the front OEM bumper from a striking vehicle.

A series of dynamic crash tests were then performed with each bumper system. The crash tests used an appropriate exemplar (identical vehicle) target vehicle for the rear bumper of the bumper system and a buck with the front bumper of the bumper system on the front. The buck was weighted so that it had the same weight as the vehicle whose front bumper was being used. The use of quasi-static force-deformation data from the force-deformation measuring apparatus in the simulation model accurately recreated the accelerations and velocities of the target and bullet vehicles measured in the crash tests [2]. The $\Delta V$ of both the target and bullet vehicles in the simulations were almost identical to the $\Delta V$ of the target and bullet vehicles measured in the crash tests.

If only the $\Delta V$ of the vehicles in a low-speed collision is off interest then the quasi-static force-deformation data measured with the quasi-static force-deformation measuring device can be used to provide the energy absorbed by both vehicles in the MER method. The analysis of crash tests indicated that essentially all of the energy absorbed in these low-speed impacts was absorbed as crush damage to the system components, the bumpers [2]. The energy absorbed at a given amount of deformation can be obtained by integrating the quasi-static force-deformation curve from zero deformation up to the chosen maximum deformation. Since the bumper system is composed of both bumpers, this integration is the energy absorbed by both vehicles minus the energy returned to the vehicles in the rebound phase of the crash, which is accounted for by the coefficient of restitution. Besides providing an accurate estimate of the crush energy, the damage created to the components in the measurement of the quasi-static force-deformation data can be compared to the damage on the components involved in the crash being investigated. This comparison provides a metric to determine the accuracy of the crush energy estimate and, ultimately, how accurate the $\Delta V$ estimate is.

Additional information and validation regarding the present methods and apparatuses can be found in [2], which is incorporated by reference in its entirety. Another example of a reconstruction method that can use data generated by the present methods and apparatuses is the Momentum-Energy-Restitution (MER) method and a description of this method can be found in [3], [4], and [5].

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] W. R. Scott, et al., *Simulation Model for Low-Speed Bumper-to-Bumper Crashes*, SAE No. 2010-01-0051 (April 2010).
[2] W. R. Scott et al., *Reconstruction of Low-Speed Crashes using the Quasi-Static Force vs. Deformation Characteristics of the Bumpers Involved in the Crashes*, SAE No. 2012-01-0598.
[3] Bailey, M. N., et al., *Data and Methods for Estimating the Severity of Minor Impacts*, SAE No. 950352, Warrendale, Pa. 15096 (April 2012).
[4] Cipriani, A. L., et al., *Low Speed Collinear Impact Severity: A Comparison Between Full Scale Testing and Analytical Prediction Tools with Restitution Analysis*, SAE No. 2002-01-0540, Warrendale, Pa. 15096.
[5] Happer, A. J., et al., *Practical Analysis Methodology for Low Speed Vehicle Collisions Involving Vehicles with Modern Bumper Systems*, SAE No. 2003-01-0492, Warrendale, Pa. 15096.

The invention claimed is:

1. An apparatus comprising:
    a frame;
    a first mount coupled in fixed relation to the frame, the first mount configured to be coupled to a first vehicle bumper;
    a second mount movably coupled to the frame, the second mount configured to be coupled to a second vehicle bumper; and
    an actuator configured to move the second mount relative to the first mount on the frame;
    where the apparatus is configured to be actuated to compress at least one of the first and second vehicle bumper between the first and second mounts.

2. The apparatus of claim 1, further comprising at least one sensor configured to detect a force applied by the actuator to at least one of the first and second mounts.

3. The apparatus of claim 2, where at least one sensor is disposed between the second mount and the actuator such that the sensor can detect a force applied to the second mount by the actuator.

4. The apparatus of claim 1, where the first and second mounts comprise at least one reinforcement bar configured to be coupled to the respective first and second vehicle bumper.

5. The apparatus of claim 1, where the second mount comprises load-bearing rollers configured to roll in contact with the frame when the second mount moves relative to the frame.

6. The apparatus of claim 1, where the frame has at least an outer dimension greater than 5 feet.

7. The apparatus of claim 1, where the actuator comprises at least one of: a hydraulic cylinder, a motor, a screw jack, a ball screw, roller screw, a hoist, a winch, a rack and pinion, a chain drive, a belt drive, a rigid chain, or a rigid belt.

8. The apparatus of claim 1, where the actuator is configured to apply a force of at least 5,000 pounds.

9. The apparatus of claim 1, where the actuator is configured to move the second mount at a rate of less than 0.1 feet per second.

10. The apparatus of claim 1, further comprising at least one displacement sensor configured to measure displacement of the second mount relative to the frame.

11. The apparatus of claim 1, where at least one image sensor is configured to record images of the apparatus.

12. The apparatus of claim 1, where at least one audio sensor is configured to detect sounds during use of the apparatus.

13. The apparatus of claim 1, further comprising a controller configured to actuate the actuators to move the mount at a rate of less than 0.1 foot per minute with a force of up to 50,000 pounds.

14. The apparatus of claim 1, further comprising a controller configured to:
    (i) apply and release a first quasi-static force to a system;
    (ii) determine whether the quasi-static force caused a permanent deformation of a component of the system;
    (iii) if the quasi-static force caused a permanent deformation, compare the permanent deformation to a reference deformation;
    (iv) if the first quasi-static force did not cause a permanent deformation or caused a permanent deformation that is less than the reference deformation, apply and release a subsequent quasi-static force to the system;
    (v) repeat steps (i)-(iii) until a permanent deformation of the component equals or exceeds the reference deformation.

15. The apparatus of claim 14, where the controller is further configured to:
    collect at least one of displacement and force data during the application and release of the quasi-static force to the system.

16. The apparatus of claim 14, where the controller is further configured to:
    collect displacement and force data corresponding to the quasi-static force that results in a permanent deformation of the component that equals or exceeds the reference deformation.

17. The apparatus of claim 16, where the controller is further configured to:
    generate a compression and rebound curve from the displacement and force data.

18. The apparatus of claim 16, where the controller is further configured to:
    determine an impact velocity using the compression and rebound curve.

19. The apparatus of claim 16, further comprising:
    determine a coefficient of restitution using the compression and rebound curve.

20. The apparatus of claim 1, where the frame is stationary during use.

21. The apparatus of claim 1, where the first mount and the second mount are movable to reconstruct an automobile collision.

\* \* \* \* \*